United States Patent
Thurmes et al.

(10) Patent No.: US 10,577,338 B2
(45) Date of Patent: Mar. 3, 2020

(54) THIADIAZOLES OR OXADIAZOLES POSSESSING ONE ALKYL, ALKENYL OR ALKYNYL TAIL AND A 4-FLUOROPHENYL OR 4-CYANOPHENYL GROUP

(71) Applicant: Citizen Finedevice Co., Ltd., Fujikawaguchiko-Machi (JP)

(72) Inventors: William Thurmes, Longmont, CO (US); Christopher Gabriel, Louisville, CO (US)

(73) Assignee: CITIZEN FINEDEVICE CO., LTD. (JP)

( * ) Notice: Subject to any disclaimer, the term of this patent is extended or adjusted under 35 U.S.C. 154(b) by 56 days.

(21) Appl. No.: 15/914,977

(22) Filed: Mar. 7, 2018

(65) Prior Publication Data

US 2019/0276418 A1  Sep. 12, 2019

(51) Int. Cl.
| | |
|---|---|
| *G02F 1/1333* | (2006.01) |
| *C07D 285/12* | (2006.01) |
| *C07D 271/107* | (2006.01) |
| *C09K 19/34* | (2006.01) |
| *C07D 417/04* | (2006.01) |
| *C07D 413/04* | (2006.01) |
| *C09K 19/02* | (2006.01) |
| *G02F 1/141* | (2006.01) |

(52) U.S. Cl.
CPC ........ *C07D 285/12* (2013.01); *C07D 271/107* (2013.01); *C07D 413/04* (2013.01); *C07D 417/04* (2013.01); *C09K 19/0225* (2013.01); *C09K 19/348* (2013.01); *C09K 19/3497* (2013.01); *G02F 1/1418* (2013.01)

(58) Field of Classification Search
CPC .............. C07D 285/12; C07D 271/107; C07D 413/04; C07D 417/04; C09K 19/348; C09K 19/3497; G02F 1/1333; G02F 1/1418
USPC ................................................... 252/299.61
See application file for complete search history.

(56) References Cited

U.S. PATENT DOCUMENTS

| | | |
|---|---|---|
| 5,849,216 A | 12/1998 | Illian et al. |
| 8,597,541 B2 | 12/2013 | Pecinovsky |
| 2008/0255203 A1* | 10/2008 | Lee ............... C07D 413/14 514/340 |

FOREIGN PATENT DOCUMENTS

| | | |
|---|---|---|
| GB | 899842 A | 6/1962 |
| WO | 2007149395 A3 | 1/2008 |

OTHER PUBLICATIONS

"Synthesis, Single Crystal Structures, and Liquid Crystal Property of 2,5-Diphenyl-1,3,4-Oxadiazoles/1,3,4-Thiadiazoles", Soft Materials, 7(4): pp. 342-354 (Year: 2009).*
Chandrakantha et al., European J. Med. Chem., vol. 45, No. 3 (2010), 1206-1210.
Dimitrowa et al., J. Prakt. Chem. 322, 933 (1980).
Karamysheva and Agafonova, Mol. Cryst. Liq. Cryst. 1999, vol. 332, 17-26.
Lee et al., J. Nanoscience and Nanotechnology, vol. 13, No. 5 (2013), 3321-3330.
Liu and Feng, Organic and Biomolecular Chem., vol. 15, No. 12 (2017), 2585-2592.
Paraschivescu et al., Tetrahedron Letters, vol. 56, No. 25 (2015), 3961-3964.
Schaefer et al., Journal fuer Praktische Chemie (Leipzig), vol. 331, No. 4 (1989), 631-636.
Sharma et al., Synthetic Comm., vol. 34, No. 13 (2004), 2387-2391.
Vachhani et al., J. Org. Chem, vol. 77, No. 19, 8768-8774 (2012).
Yang et al., Polymer (United Kingdom), vol. 55, No. 7 (2014) 1698-1706.
Zou et al., Chemistry—A European Journal, vol. 19, No. 10, (2013) 3302-3305.

* cited by examiner

*Primary Examiner* — Geraldina Visconti
(74) *Attorney, Agent, or Firm* — Elevated IP, LLC

(57) ABSTRACT

New classes of thiadiazole and oxadiazole compounds for use in LC mixtures are disclosed. In an embodiment, the new classes of thiadiazoles and oxadiazoles comprise at least one phenyl ring attached to the heterocyclic ring, where no alkyl, alkenyl or alkynyl tails are attached to the phenyl ring, but one alkyl, alkenyl or alkynyl tail is attached to the other end of the molecule, and a fluoro or cyano group appears in the para position of the phenyl ring. These compounds are disclosed as being effective at inducing smectic A phases in liquid crystal mixtures, particularly in liquid crystal mixtures also possessing a smectic C phase, more particularly in materials possessing a chiral smectic C (ferroelectric) phase.

20 Claims, No Drawings

THIADIAZOLES OR OXADIAZOLES POSSESSING ONE ALKYL, ALKENYL OR ALKYNYL TAIL AND A 4-FLUOROPHENYL OR 4-CYANOPHENYL GROUP

CROSS-REFERENCE TO RELATED APPLICATIONS

None.

BACKGROUND

Liquid crystals (LCs) have a remarkable ability to order, which is useful in electro-optical devices, such as electronic displays. In displays, for example, a thin layer of LC material is placed between glass plates and the orientation of the LC molecules is controlled by the application of an electric field with high spatial resolution. The order imparted on the LC molecules nearest the surface gets transferred through as many as 20,000 LC molecules with the result that the LC molecules furthest from the glass substrate still have the desired orientation. Ferroelectric liquid crystals (FLCs) and LCs subject to the electroclinic effect are most desirable in electro-optical devices, such as displays, switches, shutters, write heads for holographic data storage systems, and the like.

Ferroelectric liquid crystals (FLCs), which typically operate in the smectic C (SmC) phase, are most easily aligned when their SmC phase is overlaid by the nematic (N) and smectic A (SmA) phases. Thus, as the LC cools from the isotropic (I) phase, it first achieves monodirectional order in the N phase, to which is added layered order as it transitions to the SmA phase, to which is added tilted order as it transitions to the SmC phase. Hence, while FLCs require the presence of a very wide SmC phase in which to operate, they also require an N and SmA phase. Both the SmA and N phases should have a clear phase of at least 2° C., where the term "clear phase" refers to having only the desired phase, and no other coexistent phases, present in the cell over that temperature range.

To realize alignment uniform enough for display use, FLCs need not only the overlying phases, but adequate time in certain portions of the phases for the cell to reach equilibrium. For instance, with a traditional polyimide alignment layer, a very slow cooling rate is typically used throughout the SmA phase and the first few degrees of the SmC phase. That slow cooling rate would be extremely difficult to impose in a finished product. Consequently, FLC displays are typically restricted from going over any temperature that would result in a ruined product. Hence, most products containing FLC displays have both a quoted storage and operating temperature range, with the storage range being the temperature range the device can be subjected to, and the narrower operating range being the temperature range over which the device is expected to adequately perform. For most commercial purposes, a SmC to SmA transition over 90° C. is desired, and the material should retain its SmC phase down to less than −30° C., so a SmC phase width of over 120° C. is required. Having a higher SmC-SmA transition gives a clear commercial advantage.

U.S. Pat. No. 8,597,541, which is hereby incorporated by reference in its entirety, discloses that using certain types of thiadiazole compounds in mixtures, in conjunction with certain polarization-inducing components, considerably increases the polarization of LC mixtures compared with mixtures comprising the same proportion of the polarization-inducing component but lacking the thiadiazoles. In general, increasing the polarization of a mixture also increases its viscosity; the former will increase the mixture's switching speed, while the latter decreases the switching speed. Surprisingly, the polarization enhancement provided by the thiadiazoles of the '541 patent did not come with a commensurate increase in viscosity. This meant that the thiadiazole-based mixtures of the '541 patent, particularly those with a thiadiazole content comprising 30-50 weight percent of the mixture, had a faster switching speed than previous categories of FLCs. The present disclosure expands upon the work described in the '541 patent.

SUMMARY

The present disclosure generally relates to new classes of thiadiazole and oxadiazole compounds for use in LC mixtures. In an embodiment, the new classes of thiadiazoles and oxadiazoles comprise at least one phenyl ring attached to the heterocyclic ring, where no alkyl, alkenyl or alkynyl tails are attached to the phenyl ring, but one alkyl, alkenyl or alkynyl tail is attached to the other end of the molecule, and a fluoro or cyano group appears in the para position of the phenyl ring. These compounds are disclosed as being effective at inducing smectic A phases in liquid crystal mixtures, particularly in liquid crystal mixtures also possessing a smectic C phase, and more particularly in materials possessing a chiral smectic C (ferroelectric) phase.

In an aspect, a liquid crystal (LC) mixture comprises a compound of formula (I):

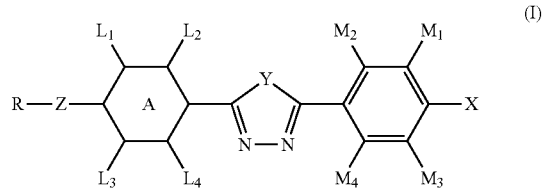

wherein X is F or CN; $M_1$, $M_2$, $M_3$, and $M_4$ are independently H or F; Y is S or O; A is phenyl, biphenyl, pyridine, pyrimidine, pyrazine or cyclohexyl; Z is a bond, O, a carbonyl group or an ester group; R is a straight-chain or branched alkyl, alkenyl or alkynyl group, optionally substituted with one or more fluorines; and $L_1$, $L_2$, $L_3$ and $L_4$ are independently H or F. In an embodiment, the LC mixture is a ferroelectric liquid crystal (FLC) mixture.

In an embodiment, an LC mixture comprises a compound of formula (I) wherein R is a straight-chain or branched alkyl, alkenyl or alkynyl group having 4 to 16 carbons, or 5 to 16 carbons, or 5 to 14 carbons, or 6 to 12 carbons, optionally substituted with one or more fluorines.

In an embodiment, an LC mixture comprises a compound of formula (I) wherein at least one of $M_1$-$M_4$ or $L_1$-$L_4$ is F.

In an embodiment, an LC mixture comprises a compound of formula (I) wherein when Z is oxygen or X is CN at least one of $M_1$-$M_4$ or $L_1$-$L_4$ is F.

In an embodiment, an LC mixture comprises a compound of formula (I) wherein X is F.

In an embodiment, an LC mixture comprises a compound of formula (I) wherein Y is S.

In an embodiment, an LC mixture comprises a compound of formula (I) wherein A is phenyl or cyclohexyl.

In an embodiment, an LC mixture comprises a compound of formula (I) wherein Z is a bond or O.

In an embodiment, the compound of formula (I) is combined with a host mixture at a concentration of at least 2 wt. %, or at least 4 wt. %, or at least 5 wt. %, or at least 10 wt. %, or at least 15 wt. %, or at least 20 wt. %, or at least 25 wt. %, or at least 30 wt. % relative to the host mixture. In an embodiment, the compound of formula (I) is combined with a host mixture at a concentration selected from 2 wt. % to 35 wt. %, or from 3 wt. % to 30 wt. %, or from 4 wt. % to 25 wt. %, or from 5 wt. % to 20 wt. %, or from 5 wt. % to 15 wt. % relative to the host mixture.

In an embodiment, addition of the compound of formula (I) to a host mixture induces a smectic A phase in an LC mixture. For example, the host mixture alone may not possess a smectic A phase.

In an embodiment, addition of the compound of formula (I) to a host mixture reduces the viscosity of the host mixture.

In an aspect, a liquid crystal display comprises at least one LC mixture disclosed herein.

In an aspect, an electronic device comprises at least one LC mixture or a liquid crystal display comprising at least one LC mixture disclosed herein.

In an embodiment, an electronic device is an electro-optic switch, a spatial light modulator, a camera, a camcorder, a projector, a cell phone, a smart phone, a tablet, a television screen, a head-mounted display, a virtual reality display, an augmented reality display, or a computer display screen.

In an aspect, the invention comprises a compound of formula (II):

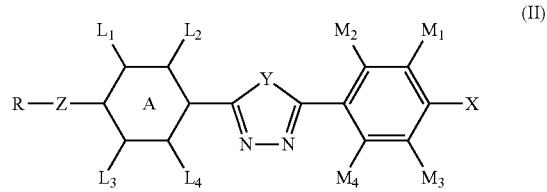

(II)

wherein X is F or CN; $M_1$, $M_2$, $M_3$, and $M_4$ are independently H or F; Y is S or O; A is phenyl, biphenyl, pyridine, pyrimidine, pyrazine or cyclohexyl; Z is a bond, O, a carbonyl group or an ester group; R is a straight-chain or branched alkyl, alkenyl or alkynyl group having 4 to 16 carbons, optionally substituted with one or more fluorines, provided that R is not tert-butyl; $L_1$, $L_2$, $L_3$ and $L_4$ are independently H or F, provided that when Z is oxygen or X is CN at least one of $M_1$-$M_4$ or $L_1$-$L_4$ is F.

In an embodiment, the invention comprises a compound of formula (II) wherein R is a straight-chain or branched alkyl, alkenyl or alkynyl group having 5 to 16 carbons, optionally substituted with one or more fluorines.

In an embodiment, the invention comprises a compound of formula (II) wherein at least one of $M_1$-$M_4$ or $L_1$-$L_4$ is F.

In an embodiment, the invention comprises a compound of formula (II) wherein X is F.

In an embodiment, the invention comprises a compound of formula (II) wherein Y is S.

In an embodiment, the invention comprises a compound of formula (II) wherein A is phenyl or cyclohexyl.

In an embodiment, the invention comprises a compound of formula (II) wherein Z is a bond or O.

In an aspect, a liquid crystal display comprises the compound of formula (I) and/or the compound of formula (II).

In an aspect, an electronic device comprises the compound of formula (I) and/or the compound of formula (II), or a liquid crystal display comprising the compound of formula (I) and/or the compound of formula (II).

In an aspect, a liquid crystal (LC) mixture comprises the compound of formula (I) and/or the compound of formula (II). In an embodiment, the LC mixture is a ferroelectric liquid crystal (FLC) mixture.

In an embodiment, the compound of formula (II) is combined with a host mixture at a concentration of at least 2 wt. %, or at least 4 wt. %, or at least 5 wt. %, or at least 10 wt. %, or at least 15 wt. %, or at least 20 wt. %, or at least 25 wt. %, or at least 30 wt. % relative to the host mixture. In an embodiment, the compound of formula (II) is combined with a host mixture at a concentration selected from 2 wt. % to 35 wt. %, or from 3 wt. % to 30 wt. %, or from 4 wt. % to 25 wt. %, or from 5 wt. % to 20 wt. %, or from 5 wt. % to 15 wt. % relative to the host mixture.

In an embodiment, addition of the compound of formula (II) to a host mixture induces a smectic A phase in an LC mixture. For example, a host mixture alone may not possess a smectic A phase.

In an embodiment, addition of the compound of formula (II) to a host mixture reduces the viscosity of the host mixture.

DETAILED DESCRIPTION

In general, the terms and phrases used herein have their art-recognized meaning, which can be found by reference to standard texts, journal references and contexts known to those skilled in the art. The following definitions are provided to clarify their specific use in the context of this description.

A "device" is a combination of components operably connected to produce one or more desired functions.

A "component" is used broadly to refer to an individual part of a device, such as a liquid crystal display of an electronic device.

"Nematic" refers to the phase of a LC characterized by arrangement of the long axes of the liquid crystal molecules in parallel lines but not layers. Thus, a nematic LC displays orientational molecular order, but not positional molecular order.

"Smectic" refers to the phase of a LC characterized by arrangement of liquid crystal molecules in layers with the long molecular axes in a given layer being parallel to one another and those of other layers and perpendicular or slightly inclined to the plane of the layer. In the "Smectic A" phase, the molecules are oriented normal to the layer plane, while in the "Smectic C" phase the molecules are tilted away from normal.

"Ferroelectric" refers to a smectic C phase of a liquid crystal with tilted layers in which the dipoles of a given layer are oriented in the same direction, and dipoles of adjacent layers are oriented in approximately the same direction, giving materials where the total macroscopic spontaneous electric polarization is non-zero.

The term "alkyl" refers to a saturated linear or branched-chain monovalent hydrocarbon radical of one to sixteen carbon atoms, wherein the alkyl radical may be optionally substituted independently with one or more substituents. Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —CH₂CH₂CH₂CH₂CH₃), 2-pentyl (—CH(CH₃)CH₂CH₂CH₃), 3-pentyl (—CH(CH₂CH₃)₂), 2-methyl-2-butyl (—C(CH₃)₂CH₂CH₃), 3-methyl-2-butyl (—CH(CH₃)CH(CH₃)₂), 3-methyl-1-butyl (—CH₂CH₂CH(CH₃)₂), 2-methyl-1-butyl (—CH₂CH(CH₃)CH₂CH₃), 1-hexyl (—CH₂CH₂CH₂CH₂CH₂CH₃), 2-hexyl (—CH(CH₃)CH₂CH₂CH₂CH₃), 3-hexyl (—CH(CH₂CH₃)(CH₂CH₂CH₃)), 2-methyl-2-pentyl (—CH(CH₃)₂CH₂CH₂CH₃), 3-methyl-2-pentyl CH(CH₃)CH(CH₃)CH₂CH₃), 4-methyl-2-pentyl (—CH(CH₃)CH₂CH(CH₃)₂), 3-methyl-3-pentyl (—C(CH₃)(CH₂CH₃)₂), 2-methyl-3-pentyl CH(CH₂CH₃)CH(CH₃)₂), 2,3-dimethyl-2-butyl (—C(CH₃)₂CH(CH₃)₂), 3,3-dimethyl-2-butyl (—CH(CH₃)C(CH₃)₃), 1-heptyl, 1-octyl, cyclopropyl, cyclobutyl, cyclopentyl, cyclohexyl, cycloheptyl, and cyclooctyl.

The term "alkenyl" refers to a linear or branched-chain monovalent hydrocarbon radical of two to sixteen carbon atoms with at least one site of unsaturation, i.e., a carbon-carbon, sp² double bond, wherein the alkenyl radical may be optionally substituted independently with one or more substituents, and includes radicals having "cis" and "trans" orientations, or alternatively, "E" and "Z" orientations. Examples include, but are not limited to, ethylenyl or vinyl (—CH═CH₂), allyl (—CH₂CH═CH₂), 1-cyclopent-1-enyl, 1-cyclopent-2-enyl, 1-cyclopent-3-enyl, 5-hexenyl, 1-cyclohex-1-enyl, 1-cyclohex-2-enyl, and 1-cyclohex-3-enyl.

The term "alkynyl" refers to a linear or branched monovalent hydrocarbon radical of two to sixteen carbon atoms with at least one site of unsaturation, i.e., a carbon-carbon, sp triple bond, wherein the alkynyl radical may be optionally substituted independently with one or more substituents. Examples include, but are not limited to, ethynyl (—C≡CH) and propynyl (propargyl, —CH₂C≡CH).

The terms "direct and indirect" describe the actions or physical positions of one component relative to another component, or one device relative to another device. For example, a component that "directly" acts upon or touches another component does so without intervention from an intermediary. Contrarily, a component that "indirectly" acts upon or touches another component does so through an intermediary (e.g., a third component).

Liquid Crystal Mixture Design

When designing FLC mixtures, many properties need to be considered, broadly separable into those dependent on chiral material, such as polarization and pitch, and those dependent on the achiral host material, such as the liquid crystalline phases and their temperature ranges, and the mixture's birefringence. Although labeling properties as achiral and chiral hints that perhaps achiral components are responsible for achiral properties and chiral components responsible for chiral properties, in fact every component of a mixture influences every property of that mixture. It is therefore highly desirable that every component of a mixture enhances the desirable properties of the mixture. Thus a component that enhances the polarization of a mixture and increases the SmA-SmC transition temperature is more desirable than the combination of one component that increases the SmA-SmC transition temperature and another that increases the mixture's polarization. This is particularly important when planning formulations of mixtures comprising at least 30% thiadiazole-containing components. The thiadiazoles are better suited to be achiral components, and indeed it was determined that while a chiral group placed on another component would have its polarization enhanced by thiadiazoles, placing the same chiral group on a thiadiazole component gave no corresponding polarization enhancement. Thus, achiral thiadiazole components were targeted.

In order to obtain FLC mixtures containing a high proportion of thiadiazole-containing components, yet having overlying N and SmA phases, thiadiazole-containing components compatible with the SmA and N phases were needed. Many tested achiral thiadiazoles strongly supported the necessary SmC phase, and most also supported the overlying N phase, but few also supported the SmA phase. In particular, those that did support the SmA phase typically did so at the expense of decreasing the SmC to SmA transition temperature, thus making it hard to reach the desired SmA-SmC transition temperature of over 90° C. Hence, thiadiazole components which supported the SmA phase while not simultaneously eroding the SmC range were needed.

Synthetic Methods

Thiadiazoles disclosed herein can be synthesized according to the methods disclosed in "Applying a Late-Stage Lawesson's Cyclization Strategy Towards the Synthesis of 1,3,4-Thiadiazole-2-Carboxylate Thioesters", Ian Thor Sutherland (2015) Thesis, Kent State.

Oxadiazoles disclosed herein can be synthesized using the same methods as the thiadiazoles, except that phosphorus pentoxide is used instead of Lawesson's reagent in the cyclization reaction.

Results and Discussion

A host mixture, based on thiadiazoles and possessing an N and a SmC but not a SmA phase, was designed and formulated.

TABLE 1

| Host Mixture (MX15069) | | |
|---|---|---|
| DTC# | Structure | Wt % |
| 950 | 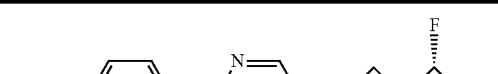 | 5.0 |
| 337 |  | 5.1 |

TABLE 1-continued

Host Mixture (MX15069)

| DTC# | Structure | Wt % |
|------|-----------|------|
| 2895 | 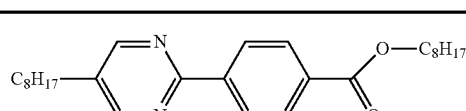 | 20.1 |
| 2957 | 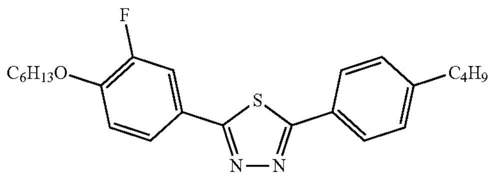 | 19.9 |
| 1671 | 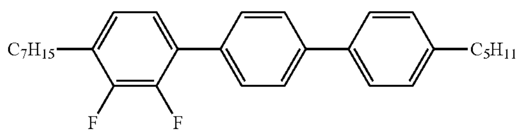 | 24.9 |
| 1965 | 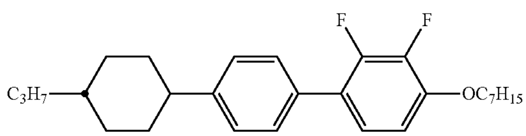 | 25.0 |

When DTC3065 was added at a 10 weight % loading to the host mixture, which possessed an N and SmC phase, but no SmA phase, it induced a SmA phase about 13° C. in width in the new mixture (MX15073). The SmC-SmA transition of the new mixture (MX15073) was about 6° C. lower than the SmC-N transition of the host mixture (MX15069), so about half of the newly induced SmA phase came at the expense of the top end of the SmC phase. The rotational viscosity of MX15073 versus MX15069 dropped by about 25%. The polarization of MX15073 versus MX15069 dropped by about 15%.

As a comparison, DTC2485, another compound known to induce the SmA phase in mixtures, was added at a 10 weight % loading to MX15069 to create MX15071. In this mixture, a SmA phase was indeed induced, but the SmC-SmA transition was over 20° C. lower than the SmC-N transition in MX15069. The viscosity of MX15071 is similar to that of MX15073, dropping 25% from that of the host mixture (MX15069). MX15071's polarization dropped by 25% compared to the host mixture (MX15069), and its driven cone angle at 25° C. with a 1.65V 250 Hz square wave is about 20.2°, lower than that of MX15073 (23.1°) or MX15069 (23.4°).

TABLE 2

Liquid crystalline properties of disclosed compounds (° C.)

| DTC# | (I) → N | → SmA | → SmC | → Sx | → Cr | SmA width | Structure |
|------|---------|-------|-------|------|------|-----------|-----------|
| 2485 | | 47.7 | | 30.9 | 16.8 | | 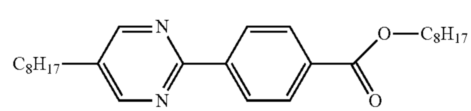 |
| 3062 | 227 | 205 | | 142 | 63 | | 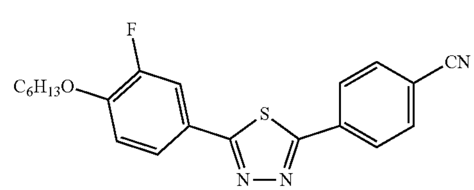 |

TABLE 2-continued

| | | | | | SmA | |
|---|---|---|---|---|---|---|
| DTC# | (I) → N | → SmA | → SmC | → Sx | → Cr width | Structure |
| 3063 | | 194.1 | | | 63 131.1 | C₆H₁₃O–[3-F-phenyl]–[thiadiazole]–[4-F-phenyl] |
| 3065 | | 108.7 | | | 80 28.7 | C₈H₁₇–[phenyl]–[thiadiazole]–[4-F-phenyl] |
| 3066 | | 126.7 | | 77.6 | 49.1 | C₆H₁₃O–[3-F-phenyl]–[thiadiazole]–[3-F-phenyl] |
| 3069 | | | | 85 | 0 | [phenyl]–[thiadiazole]–[cyclohexyl]–C₅H₁₁ |
| 3070 | 105.6 | | [56.6] | 82.3 | 0 | 4-F-benzoate ester–[2-F-phenyl]–[thiadiazole]–C₈H₁₇ |
| 3071 | 142.9 | 121.5 | 119 | | 2.5 | 4-F-phenyl–[thiadiazole]–[cyclohexyl]–C₅H₁₁ |
| 3072 | 103.5 | | | 100 | 0 | C₈H₁₇O–[3-F-phenyl]–[thiadiazole]–[phenyl] |
| 3074 | 147 | 119 | 102 | 97 | 17 | C₈H₁₇O–[3-F-phenyl]–[thiadiazole]–[2,4-diF-phenyl] |

TABLE 2-continued

Liquid crystalline properties of disclosed compounds (° C.)

| DTC# | (I) → N | → SmA | → SmC | → Sx | → Cr | SmA width | Structure |
|---|---|---|---|---|---|---|---|
| 3075 | | 157.8 | 100.8 | | 57 | | 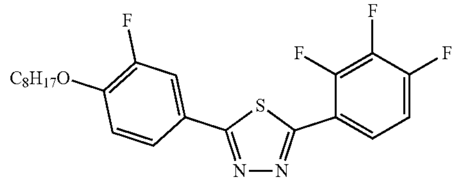 |
| 3076 | 129.5 | | | | 108 | 0 | 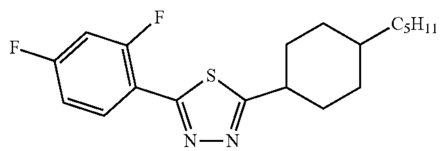 |
| 3077 | 114.5 | | | | 108 | 0 | 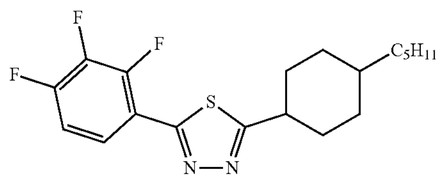 |
| 3119 | | | | | 106.1 | 0 | 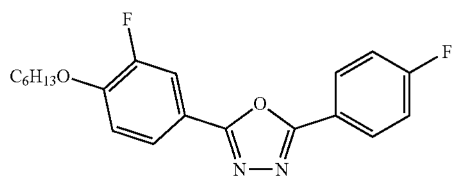 |
| 3120 | 97 | | | | 59.1 | 0 | 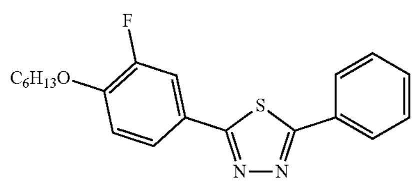 |
| 3121 | | | | | 70.6 | 0 | 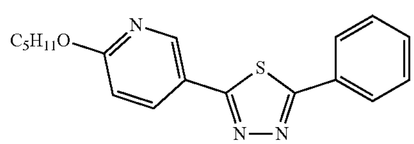 |
| 3122 | | 207.2 | | | 81.8 | 125.4 | 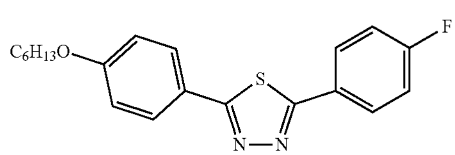 |
| 3123 | 176.8 | 173 | | | 117.9 | 55.1 | 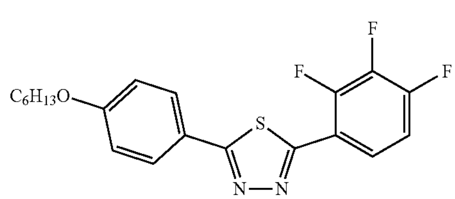 |
| 3124 | 171.9 | | | | 90.6 | 0 | 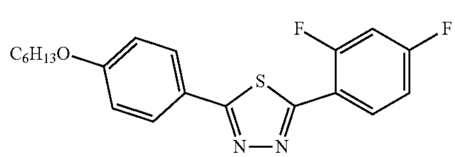 |

TABLE 2-continued

Liquid crystalline properties of disclosed compounds (° C.)

| DTC# | (I) → N | → SmA | → SmC | → Sx | → Cr | SmA width | Structure |
|---|---|---|---|---|---|---|---|
| 3126 | 201.8 | | | 101.7 | 100.1 | | 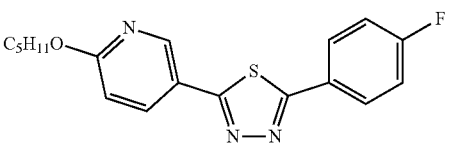 |
| 3128 | 169.5 | | 107.2 | 95.2 | 0 | | 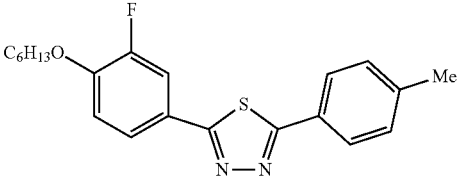 |
| 1358 | 194 | 171.6 | 110 | 102.5 | 61.6 | | 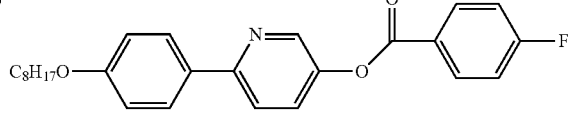 |

TABLE 3

Liquid crystalline properties of mixtures of MX15069 and dopants (10 wt %)

| MX# | DTC# | (I) → N | → SmA | → SmC | SmA width | ΔI-? | Δ→SmC | Ps | V | ERT | Cone ∠ | Av T95 |
|---|---|---|---|---|---|---|---|---|---|---|---|---|
| 15069 | — | 141.8 | | 108.4 | | | | 65.4 | 269 | 113 | 46.8 | 280 |
| 15070 | 3063 | 143.6 | 125 | 105.3 | 19.7 | 1.8 | −3.1 | 60.9 | 262 | 114 | 46.8 | 171 |
| 15071 | 2485 | 127.7 | 109.5 | 88.3 | 21.2 | −14.1 | −20.1 | 49.2 | 199 | 100 | 40.4 | 104 |
| 15072 | 3062 | | 157.2 | 89.0 | 68.2 | 15.4 | −19.4 | 55.2 | 266 | 112 | | |
| 15073 | 3065 | 135.7 | 115.5 | 102.3 | 13.2 | −6.2 | −6.1 | 56.5 | 198 | 114 | 46.3 | 182 |
| 15074 | 3066 | 136.7 | 109.6 | 105.4 | 4.2 | −5.1 | −3 | 55.4 | 265 | 158 | 35.4 | 292 |
| 15075 | 3069 | 136.1 | 103.3 | 96.3 | 7 | −5.7 | −12.1 | 58.6 | 218 | 115 | 29.6 | 412 |
| 15076 | 3071 | 143.5 | 125.0 | 94.3 | 30.7 | 1.7 | −14.1 | 58.9 | 234 | 93.5 | 37.3 | 190 |
| 15077 | 3072 | 139.1 | | 101.5 | 0 | −2.8 | −6.9 | 64.4 | 300 | 174 | 21.1 | 466 |
| 15078 | 3074 | 140.7 | | 108.4 | 0 | −1.2 | 0 | 55.2 | 255 | 160 | 21.9 | 525 |
| 15079 | 3075 | 140.7 | 119.5 | 110.2 | 9.3 | −1.1 | 1.8 | 51.2 | 254 | 158 | 45.9 | 252 |
| 15080 | 3076 | 140.3 | 109.6 | 99.5 | 10.1 | −1.5 | −8.9 | 56 | 212 | 112 | 24 | 468 |
| 15081 | 3077 | 139.6 | 117.7 | 94.3 | 23.4 | −2.2 | −14.1 | 54.6 | 230 | 117 | 46.2 | 156 |
| 15082 | 3119 | 131.7 | 105.8 | 93.9 | 11.9 | −10.1 | −14.5 | 53.5 | 209 | 117 | 44.7 | 146 |
| 15106 | 3120 | 137.2 | | 98.5 | 0 | −4.6 | −9.9 | 58.2 | 190 | 156 | 30.8 | 369 |
| 15107 | 3121 | 135.6 | | 97.2 | 0 | −6.3 | −11.2 | 58.2 | 174 | 131 | 25.5 | |
| 15108 | 3070 | 138.3 | | 104.5 | 0 | −3.5 | −3.9 | 55.0 | 207 | 115 | 18.7 | 397 |
| 15136 | 3122 | 145.9 | 126.6 | 106.9 | 19.7 | 4.1 | −1.5 | 61 | 269 | 132 | 42.7 | 167 |
| 15137 | 3123 | 142.8 | 117.6 | 106.7 | 10.9 | 1 | −1.7 | 54.5 | 255 | 153 | 36.5 | 165 |
| 15138 | 3124 | 142.8 | | 107.1 | 0 | 1 | −1.3 | 56.1 | 255 | 148 | 13.6 | 322 |
| 15139 | 1358 | 146.1 | | 111 | | 4.2 | 2.6 | 55 | 215 | 120 | 36.3 | 188 |
| 15140 | 3128 | 143.3 | | 105.6 | | 1.4 | −2.8 | 62 | 250 | 110 | 31.3 | 181 |
| 15142 | 3126 | 142.4 | 126.3 | 102.1 | 24.2 | .6 | −6.3 | 59.9 | 327 | 122 | 42.9 | 171 |

Explanation of columns in Table 3: All temperatures are given in ° C.; column 3 shows the temperature of the cooling transition into the N phase, if the mixture has an N phase; columns 4 and 5 show similar transition temperatures for entering the SmA and SmC phases respectively; column 6 shows the width of the mixture's SmA phase; column 7 compares the doped mixture to the host mixture (MX15069), showing the change in temperature of the transition from the isotropic into the top liquid crystalline phase; column 8 similarly shows the change in the top of the SmC range between the two mixtures; Ps=spontaneous polarization, given in nC/cm²; V=rotational viscosity, in millipoise seconds; ERT=electric rise time, the 10-90% rise time as measured dielectrically; Cone gives the cone angle of the mixture in a 0.7 μm thick cell with ITO electrodes and a brushed polyimide alignment layer, driven with ±1.65V; T95 is the optical 0-95% rise time.

A comparison of the series DTC3120, DTC3063, DTC3074, and DTC3075, in which the non-alkylated phenyl ring has from 0 to 3 fluorines on it, is instructional. When doped into MX15069, they give mixtures MX15106, MX15070, MX15078, and MX15079 respectively. These mixtures have SmA widths of 0, 19.7, 0, and 9.3° C., respectively. Thus, having a single fluorine in the para position on that phenyl ring results in the compound being a more effective SmA promoter than having three fluorines on the ring, and is much more effective than having zero or two fluorines on the ring. All three compounds with fluorine on that ring help preserve the top end of the SmC phase. DTC3062, aside from the non-alkylated phenyl ring, has a structure identical to the other four compounds mentioned in this paragraph, but has a cyano group on that ring. This compound very strongly promoted the SmA phase, giving a SmA phase over 65° C. wide when doped into the host mixture.

It is also interesting to compare the series DTC3069, DTC3071, DTC3076, and DTC3077, in which the non-alkylated phenyl ring has 0 to 3 fluorines on it. When doped into MX15069, these dopants gave mixtures MX15075, MX15076, MX15080, and MX15081 respectively. These mixtures have SmA widths of 7, 30.7, 10.1, and 23.4° C. respectively. This series of dopants and mixtures gives a clearer picture, compared to the previously mentioned series, of the relative effects of adding fluorines to the non-alkylated phenyl ring and their ability to induce a SmA phase in the host mixture: one fluorine in the para position gives the strongest induction of a SmA phase in the host mixture; having three fluorines on that ring gives a dopant that is about ⅔ as effective; having two fluorines on that ring gives a dopant that is about ⅓ as effective as the single-fluorine compound; having no fluorines on that ring gives a dopant that is about ¼ as effective as the single-fluorine compound.

The performance of DTC1358 and DTC3128 in the host mixture (MX15069) is also instructive. DTC1358 incorporates several of the structural features of the class of compounds disclosed herein, namely a phenyl ring with a fluorine in the para position, a long alkoxy tail at the other end of the molecule, and three rings in the core. It also possesses a wide SmA phase, hinting that its inclusion in a mixture might impart a SmA phase to the mixture, but the lack of a SmA phase in MX15139 shows that it is not effective at imparting a SmA phase to the mixture. DTC3128 is also similar to the class of compounds disclosed herein, but instead of a para-fluorine on the phenyl ring, it has a methyl group, which is slightly lamer than a fluorine atom. Its similarity to the claimed structures might be expected to impart a SmA phase to the host mixture (MX15069), but no such SmA phase occurred in MX15141.

STATEMENTS REGARDING INCORPORATION BY REFERENCE AND VARIATIONS

All references cited throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the invention has been specifically disclosed by preferred embodiments, exemplary embodiments and optional features, modification and variation of the concepts herein disclosed can be resorted to by those skilled in the art, and that such modifications and variations are considered to be within the scope of this invention as defined by the appended claims. The specific embodiments provided herein are examples of useful embodiments of the invention and it will be apparent to one skilled in the art that the invention can be carried out using a large number of variations of the devices, device components, and method steps set forth in the present description. As will be apparent to one of skill in the art, methods and devices useful for the present methods and devices can include a large number of optional composition and processing elements and steps. All art-known functional equivalents of materials and methods are intended to be included in this disclosure. Nothing herein is to be construed as an admission that the invention is not entitled to antedate such disclosure by virtue of prior invention.

When a group of substituents is disclosed herein, it is understood that all individual members of that group and all subgroups are disclosed separately. When a Markush group or other grouping is used herein, all individual members of the group and all combinations and subcombinations possible of the group are intended to be individually included in the disclosure.

It must be noted that as used herein and in the appended claims, the singular forms "a", "an", and "the" include plural reference unless the context clearly dictates otherwise. Thus, for example, reference to "a display" includes a plurality of such displays and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are described.

Whenever a range is given in the specification, for example, a range of integers, a temperature range, a time range, a composition range, or concentration range, all intermediate ranges and subranges, as well as all individual values included in the ranges given are intended to be included in the disclosure. As used herein, ranges specifically include the values provided as endpoint values of the range. As used herein, ranges specifically include all the integer values of the range. For example, a range of 1 to 100 specifically includes the end point values of 1 and 100. It will be understood that any subranges or individual values in a range or subrange that are included in the description herein can be excluded from the claims herein.

As used herein, "comprising" is synonymous and can be used interchangeably with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" can be replaced with either of the other two terms. The invention illustratively described herein suitably can be practiced in the absence of any element or elements, limitation or limitations which is/are not specifically disclosed herein.

What is claimed is:

1. A liquid crystal (LC) mixture comprising a compound of formula (I):

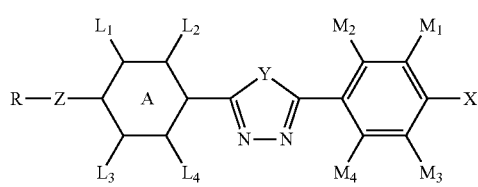

wherein
X is F or CN;
$M_1$, $M_2$, $M_3$, and $M_4$ are independently H or F;
Y is S;
A is phenyl, biphenyl, pyridine, pyrimidine, pyrazine or cyclohexyl;
Z is a bond, O, a carbonyl group or an ester group;
R is a straight-chain or branched alkyl, alkenyl or alkynyl group, optionally substituted with one or more fluorines; and
$L_1$, $L_2$, $L_3$ and $L_4$ are independently H or F,
wherein the compound of formula (I) is combined with a host mixture.

2. The LC mixture of claim 1, wherein the LC mixture is a ferroelectric liquid crystal (FLC) mixture.

3. The LC mixture of claim 1, wherein R is a straight-chain or branched alkyl, alkenyl or alkynyl group having 4 to 16 carbons, optionally substituted with one or more fluorines.

4. The LC mixture of claim 1, wherein R is a straight-chain or branched alkyl, alkenyl or alkynyl group having 5 to 16 carbons, optionally substituted with one or more fluorines.

5. The LC mixture of claim 1, wherein at least one of $M_1$-$M_4$ or $L_1$-$L_4$ is F.

6. The LC mixture of claim 1, wherein when Z is oxygen or X is CN at least one of $M_1$-$M_4$ or $L_1$-$L_4$ is F.

7. The LC mixture of claim 1, wherein X is F.

8. The LC mixture of claim 1, wherein A is phenyl or cyclohexyl.

9. The LC mixture of claim 1, wherein Z is a bond or O.

10. The LC mixture of claim 1, wherein the compound of formula (I) is combined with the host mixture at a concentration of at least 2 wt. % relative to the host mixture.

11. The LC mixture of claim 1, wherein the compound of formula (I) is combined with the host mixture at a concentration selected from 2 wt. % to 35 wt. % relative to the host mixture.

12. The LC mixture of claim 1, wherein addition of the compound of formula (I) to the host mixture induces a smectic A phase in the LC mixture.

13. The LC mixture of claim 1, wherein addition of the compound of formula (I) to the host mixture reduces the viscosity of the host mixture.

14. A liquid crystal display comprising the LC mixture of claim 1.

15. An electronic device comprising the LC mixture of claim 1, or the liquid crystal display of claim 14.

16. The electronic device of claim 15, wherein the electronic device is an electro-optic switch, a spatial light modulator, a camera, a camcorder, a projector, a cell phone, a smart phone, a tablet, a television screen, a head-mounted display, a virtual reality display, an augmented reality display, or a computer display screen.

17. A compound of formula (II):

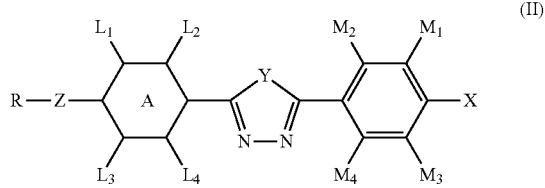

wherein
X is F or CN;
$M_1$, $M_2$, $M_3$, and $M_4$ are independently H or F;
Y is S;
A is phenyl, biphenyl, pyridine, pyrimidine, pyrazine or cyclohexyl;
Z is a bond, O, a carbonyl group or an ester group;
R is a straight-chain or branched alkyl, alkenyl or alkynyl group having 4 to 16 carbons, optionally substituted with one or more fluorines, provided that R is not tert-butyl;
$L_1$, $L_2$, $L_3$ and $L_4$ are independently H or F, provided that when Z is oxygen or X is CN at least one of $M_1$-$M_4$ or $L_1$-$L_4$ is F.

18. An electronic device comprising the compound of claim 17.

19. A liquid crystal (LC) mixture comprising the compound of claim 17.

20. The electronic device of claim 18, wherein the electronic device is an electro-optic switch, a spatial light modulator, a camera, a camcorder, a projector, a cell phone, a smart phone, a tablet, a television screen, a head-mounted display, a virtual reality display, an augmented reality display, or a computer display screen.

* * * * *